United States Patent [19]

Juvinall

[11] Patent Number: 4,644,151

[45] Date of Patent: Feb. 17, 1987

[54] IDENTIFICATION OF A MOLDED CONTAINER WITH ITS MOLD OF ORIGIN

[75] Inventor: John W. Juvinall, Ottawa Lake, Mich.

[73] Assignee: Owens-Illinois, Inc., Toledo, Ohio

[21] Appl. No.: 720,336

[22] Filed: Apr. 5, 1985

[51] Int. Cl.⁴ .............................................. G01D 5/36
[52] U.S. Cl. ................................ 250/223 B; 356/240; 235/494
[58] Field of Search .......................... 250/223 B, 566; 356/240; 235/454, 462, 466, 490, 494

[56] References Cited

U.S. PATENT DOCUMENTS

4,201,338  5/1980  Keller ......................... 250/223 B X

Primary Examiner—Eugene R. LaRoche
Assistant Examiner—Robert J. Pascal
Attorney, Agent, or Firm—John R. Nelson

[57] ABSTRACT

A method and system for identifying a molded container such as a glass bottle with its mold of origin, and a corresponding container. Each container has molded therein a plurality of indicia in the form of surface bumps or protrusions extending in an arcuate array at uniformly spaced indicia positions around the container heel perpendicularly of the container axis. The indicia are grouped in sets of two adjacent indicia positions, the sets being of two mutually unique configurations, whereby the sets as a whole identify a binary code associated with the container mold of origin. The method and system for reading such code in accordance with the disclosure contemplate directing a source of diffused light energy onto the container heel, with such energy having an intensity gradient at predetermined orientation with respect to the container axis. A camera is positioned to receive light energy reflected by the heel and is monitored to read the coded indicia as a function of alternation of the normal reflection pattern by the bumps or protrusions.

16 Claims, 16 Drawing Figures

IDENTIFICATION OF A MOLDED CONTAINER WITH ITS MOLD OF ORIGIN

The present invention is directed to inspection of molded containers, and more particularly to a method and system for identifying a molded container such as a glass bottle or jar with its associated mold of origin.

BACKGROUND OF THE INVENTION

Defects in molded containers such as glass bottles and jars are often related to defects in the associated mold of origin. For this reason, it is desirable in an automated operation having a plurality of molds to possess the ability to identify a specific molded container with its mold of origin. The defective mold may then be shut down for repair while the remaining molds continue operation. Alternatively, containers from the defective mold may be automatically sorted as they proceed down the production line.

Mold identification is generally accomplished by molding a mold-identifying code into each container during the forming process. This code may then be read by a suitable scanner for identifying the container with its mold of origin. A number of optical techniques, which find particular utility in conjunction with glass containers, have been proposed for encoding and later reading of the mold-identifying code. For example, in U.S. Pat. No. 3,745,314, light is transmitted axially through a stationary container while the image of a code molded onto the container bottom is rotated past a reading station positioned beneath the container. Encoding and scanning systems which are generally similar in basic concept are illustrated in U.S. Pat. Nos. 3,963,918 and 3,991,883, and in published UK Application Nos. 2,033,120 and 2,017,892. In general, these techniques rely upon refraction of light passing through the code bumps or "lenses," and thus on the optical transmission characteristics of the container material, embody moving optical elements which do not have desired reliability, and/or require the use of end codes on the container for indicating beginning and end of the code to be read. One embodiment disclosed in U.S. Pat. No. 3,963,918 directs light from a rotating light source onto a code molded into the bottom of a container and reads the container code as a function of light energy reflected from the code bumps.

UK Pat. No. 1,580,735 discloses a method and system for mold identification wherein the mold-identifying code is molded into the heel of the container, i.e. at the junction of the container side wall and bottom, as a series of raised integral dot or bar bumps disposed in parallel rows or tracks perpendicular to the container axis. Light energy is transmitted through the container as the latter is rotated about its axis. A scanner is positioned to receive light energy transmitted through the heel of the rotating container. One of the parallel tracks is treated as a timing track to control reading of code data represented in the other track, and the code is read as a function of the refractive characteristic of the timing and code bumps in the adjacent tracks. Again, start and end codes are employed to indicate beginning and end of a scanning operation.

U.S. Pat. Nos. 4,175,236 and 4,230,266 disclose a mold identification technique wherein the mold-identifying code is molded into the container bottom as concentric rings at preselected spacing. A source of diffused light energy is directed through a gradient filter and a lens onto the bottom of the container, with the gradient filter being such that the intensity of light varies linearly as a function of angle of incidence on the container bottom. A camera, which includes an array of photocells parallel to the filter gradient, is positioned to receive light reflected from the container bottom as the container passes over the scanning system, and the mold-specific code is read as a function of the rate of change of light intensity reflected by the leading and trailing edges of the rings.

OBJECTS AND SUMMARY OF THE INVENTION

A general object of the present invention is to provide an improved technique for encoding molded containers with a code specific to the mold of origin and for reading such code, which technique is economical to implement, reliable in operation, requires use of only a small portion of the container, and is insensitive to other indicia such as raised lettering on the container.

A further and more specific object of the invention is to provide a method of so encoding a molded container with indicia identifying the mold of origin, a molded container so encoded, a method of reading the mold-identifying codes on containers so encoded, and a system embodying such method.

Yet another object of the invention is to provide a method and apparatus for optically scanning the container code which overcomes problems associated with internal reflections and refractions of light energy within the container wall.

In accordance with specific embodiments of the invention herein disclosed, the containers are encoded during the molding operation with code indicia consisting of raised elements—i.e. bumps or bars—extending around the heel of the container in an arcuate array perpendicular to the container axis. The code elements are arrayed in mutually unique sets representing binary information which depends upon sequence of elements within the sets. In the preferred embodiments, each set consists of two indicia zones or positions, with the binary code for each set being a function of the sequence of differing elements are each indicia position, or the presence of a single element at one or the other indicia position.

A system and method for reading such code contemplate a source of semi-diffused light energy directed onto the container heel as the container is rotated or otherwise moved in the direction of the indicia array, with the light energy source having an intensity gradient at predetermined orientation with respect to the container axis. A camera, which includes a linear array of light sensitive elements coplanar with the container axis, is positioned to view the illuminated container heel. Individual code elements are detected as a function of light energy reflected by an edge of each element. Following a complete container scan, consisting of one container revolution, the detected by the camera is correlated to locate the code array, identify individual element sets, and then identify the code represented by all sets.

BRIEF DESCRIPTION OF THE DRAWINGS

The invention, together with additional objects, features and advantages thereof, will be best understood from the following description, the appended claims and the accompanying drawings in which:

DETAILED DESCRIPTION

Figures 1, 2A, 2B:
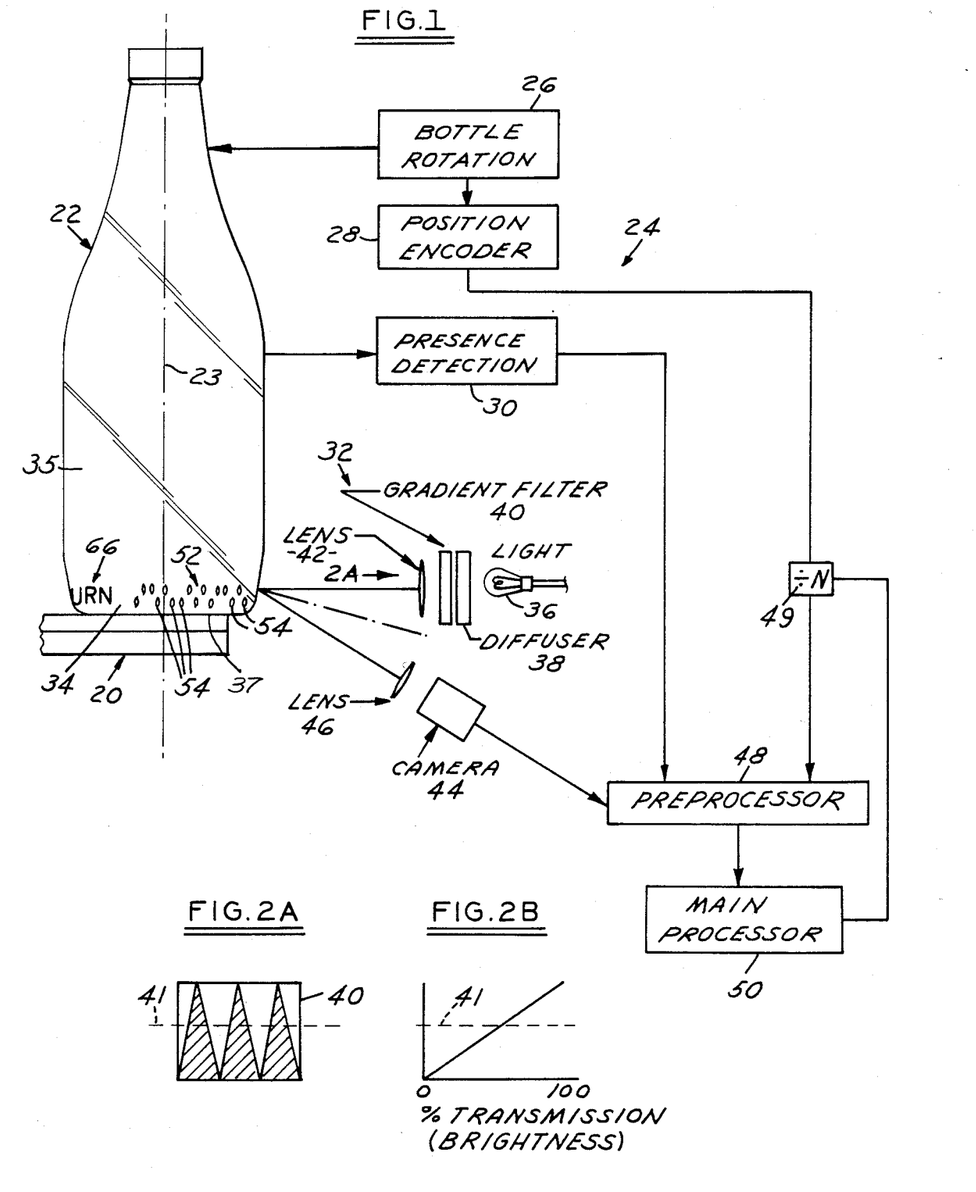
FIG. 1 is a schematic diagram of a system for scanning and reading mold-identifying codes on containers encoded in accordance with the invention.
FIGS. 2A and 2B illustrate the transmission characteristics of the gradient filter employed in the system of FIG. 1, FIG. 2A being taken from the direction 2A in FIG. 1.

Referring to FIG. 1, a conveyor, typically including a starwheel (not shown) with a slide plate 20, is so disposed and connected to a source of molded containers as to bring successive containers 22 into position at a code read station 24. Conveyor 20 may be of any suitable type, such as those shown in U.S. Pat. Nos. 4,230,219 or 4,378,493, the disclosures of which are incorporated herein by reference, and would typically include a rotatable starwheel for bringing successive containers into position and holding the containers in fixed position during the scanning operation. A drive roller or the like 26 is positioned to engage container 22 at station 24 and to rotate the container about its central axis 23. An encoder 28 is coupled to the container rotation mechanism to provide signals indicative of increments of container rotation. In the preferred implementation of the invention herein disclosed, container 22 comprises a molded glass bottle. A detector 30 such as a limit switch is positioned to provide a signal indicative of presence of container 22 at station 24.

A source 32 of semi-diffused light energy is directed onto the region of the heel 34 of container 22—i.e., onto that portion of the container side wall 35 contiguous with the bottom load-bearing surface 37. Source 32 includes one or more lamps 36, a diffuser plate 38, a gradient filter 40 and a lens 42 for directing light energy from lamp 36 transmitted through plate 38 and filter 40 onto container heel 34. Filter 40 (FIGS. 1 and 2) has a linear attenuation gradient which varies axially of container 22 (FIG. 2A) from zero attenuation (one hundred percent transmission) at the upper filter edge to full attenuation (zero transmission) at the lower edge (FIG. 2B).

A camera 44 is positioned beneath light source 32 and comprises a plurality of individual light sensitive elements disposed in a linear array which is coplanar with the axis of container 22. Preferably, camera 44 includes a linear array of sixteen elements (e.g., elements 1-16 in FIG. 7). A lens 46 is positioned before camera 42 so as to focus the camera array onto a field of view which comprises a narrow strip of the container heel coplanar with and at an acute angle to the container axis. In general, the angle between the source and camera is maintained as small as possible. A preprocessor 48 receives signals from each of the elements of camera 44, from container presence detector 30, and from rotation encoder 28 through a divide-by-N counter 49. In general, the purpose of preprocessor 48 is to monitor the various input signals in real time, to compress input information into a form indicative of possible code data, and to transmit such compressed data to a primary or main processor 50 for analysis. Operation of preprocessor 48 and main processor 50 will be described in greater detail hereinafter.

Figure 3:
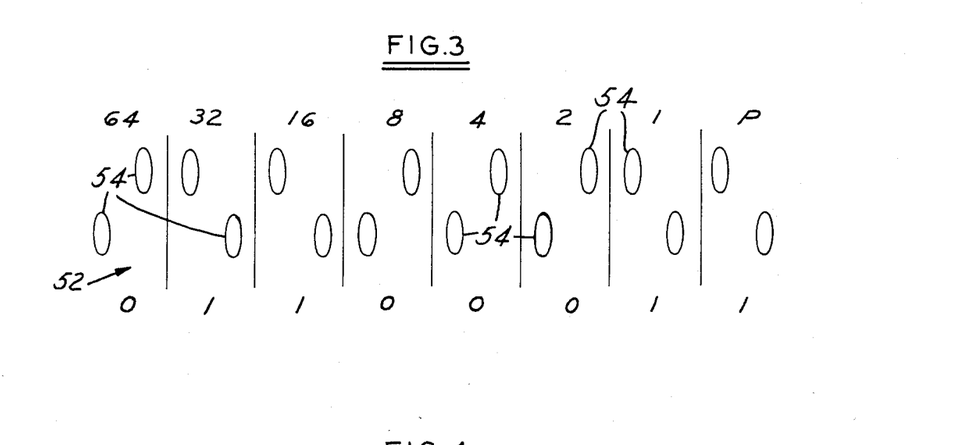
FIGS. 3-6 illustrate respective embodiments of the encoding scheme of the invention, the scheme of FIG. 6 being preferred.

In accordance with the embodiments of the invention herein disclosed, each container 22 is provided with a code 52 on the container heel 34 for identifying the mold of container origin. Code 52 comprises plurality of irregularities, such as for example, bumps or protrusions 54 integrally molded into the container heel at uniformly spaced circumferential positions in an arcuate array perpendicular to the container axis. FIGS. 1 and 3 illustrate an embodiment of the invention wherein each bump 54 comprises a generally oval bar having a longitudinal dimension coplanar with the axis 23. Bars 54 are grouped in sets of two axially offset from each other, i.e., both still coplanar but at different axial or vertical positions in the direction of the central axis. Each set is identical to the remaining sets or the lateral mirror image thereof. Thus, all bars 54 are grouped in paired sets of two unique configurations, one of which may be considered to designate a binary "one" and the other to designate a binary "zero".

Referring to FIG. 3, code 52 is illustrated in the form of eight paired sets. The right-hand pair set in FIG. 3 is designated by the letter P and is indicative of a binary parity bit. The succeeding sets, from right to left, are coded binary bits indicative of the associated $2^n$ decimal values one through sixty-four respectively. In the particular embodiment illustrated, a low bar followed by a high bar, moving from right to left, is interpreted as a binary "one", while a high bar followed by a low bar is indicative of a binary "zero". Thus, a binary "one" code at the one, sixteen and thirty-two positions, and a binary zero at the two, four, eight and sixty-four position, indicate a decimal mold-identifying code of forty-nine. A "one" bit in the P position indicates even parity.

Figure 4:
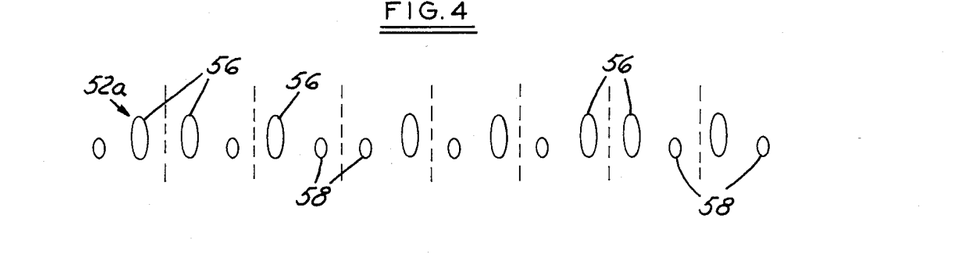
Figure 5:
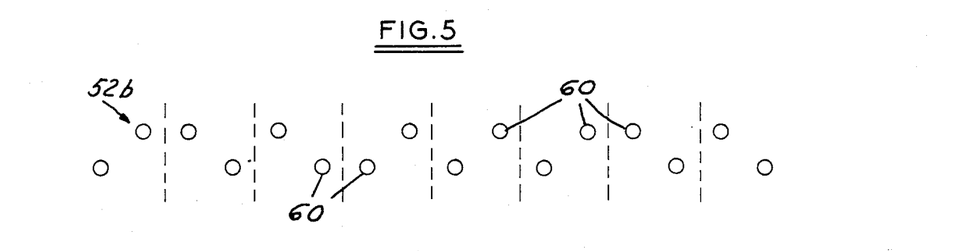

FIGS. 4 and 5 illustrate alternative embodiments 52a and 52b of code 52. The binary and decimal values associated with the code sets of FIGS. 4 and 5 are identical to those of FIG. 3, and FIGS. 4 and 5 are aligned vertically with FIG. 3 for purposes of comparison. In FIG. 4, code 52a comprises a plurality of long and short bars 56,58 arranged in paired sets of one long bar and one short bar, different dimensional characteristics, with the sequence of bars within a given set being indicative of a binary "one" or "zero". In FIG. 5, code 52b includes a plurality of dot-like bumps 60 arranged in sets of two and axially offset from each other.

Figure 6:
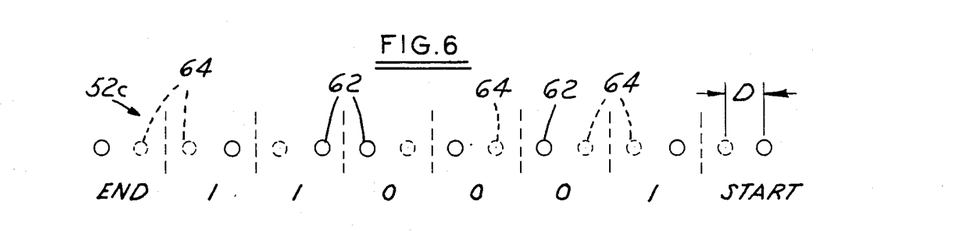

FIG. 6 illustrates a preferred embodiment 52c of code 52 in accordance with the invention. FIG. 6 is aligned vertically with FIGS. 3-5 for purposes of comparison. In FIG. 6, the code 52 comprises a circumferential array of irregularities or dot-like bumps 62 similar to the bumps 60 in FIG. 5. However, in the embodiment of FIG. 6, the bumps 62 are not grouped in paired sets to be axially offset or dimensionally different from each other as in FIGS. 3–5. Instead, each set has only one bump 62 at either one of the circumferential positions laterally aligned and paired with an empty space at the other circumferential position, as illustrated by the phantom representation 64 in each set. Since, in the embodiment of FIG. 6, the sets or code bits are represented by a bump 62 and an empty space 64, rather than by two dots or bars as in FIGS. 3–5, it is necessary to provide start and end code bits. Thus, the embodiment of FIG. 6 does not include a sixty-four bit or a parity bit, although such could be added by merely lengthening the code in the circumferential direction.

Operation of the invention for scanning and reading the mold-identifying code on each bottle will be described in connection with FIGS. 7–11 and 13. In general, the individual surface irregularities which collectively comprise the code, specifically bumps 62 of code 52c (FIG. 6), are detected as a function of disturbance or variation of the normal pattern of light reflection from the container heel as the camera "sweeps" the code—i.e., as the code is moved past the stationary camera and light source. Normally, the individual camera photocells view a generally gray field at the intensity of the mid-line 41 (FIGS. 2A and 2B) of gradient filter 40 (FIG. 1). However, the upper and lower sloping surfaces of each bump 62 reflect the field of view of one (or more) photocells upwardly or downwardly of filter 40, i.e. in the direction of the filter gradient, so that the intensity or brightness "seen" by that photocell is greater or less than that "seen" by adjacent photocells whose field of view is not so reflected. The system electronics scan the photocell array (elements 1–16 in FIG. 7) of camera 44 at increments of container rotation (scan increments in FIG. 9), identify the code elements or bumps 62 as "bright spots" in the swept field, and thereby determine the code represented by the code elements and the spacing therebetween.

Figures 7, 8:
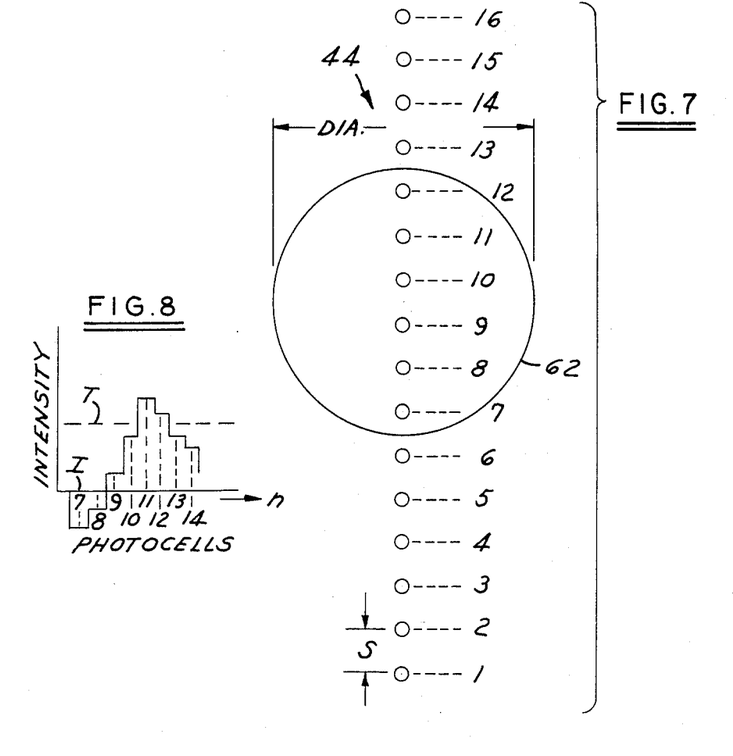
FIG. 7 is a magnified view of a code element (FIG. 6) with camera field of view superimposed thereon, which is useful in explaining operation of the invention.
FIG. 8 is a graphic illustration of operation of FIG. 7.
Figures 9, 10, 13:
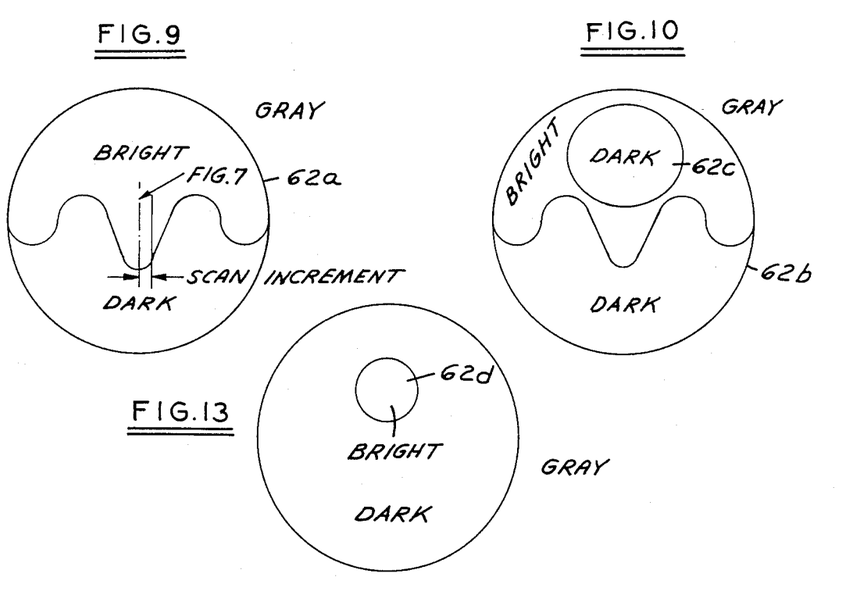
FIG. 9 is a schematic illustration of a normal code element image as "viewed" by the camera in successive scans.
FIG. 10 is a similar schematic illustration of a code element image which is marginal for detection purpose.
FIG. 13 is a schematic illustration similar to those of FIGS. 9 and 10 illustrating a code element image which is marginal for detection purposes.

FIG. 7 illustrates the field of view of the sixteen photocells of camera 44 superimposed upon a code bump 62 at a scan which centers upon the code bump. FIG. 8 illustrates the light intensity or brightness pattern seen by camera photocells 7–14 for the specific scan of FIG. 7, and FIG. 9 illustrates the overall image 62a of bump 62 seen by camera 44 as the camera sweeps the bump. Preprocesser 48 (FIG. 1) sequentially scans or sweeps each of the light sensitive photocells 1–16 in camera 44 at each increment of container rotation sensed by encoder 28 and counter 49. When no code indicia bump is within the camera field of view, all camera elements sense a gray background intensity I (FIGS. 8 and 9). However, when a code indicia bump 62 moves into the camera field of view, the slope of the bump top edge disturbs this normal reflectance pattern, intensifying light energy seen at some elements while reducing the intensity seen at other elements. In the particular scan of FIGS. 7 and 8, the upper slope of bump 62 reflects the field of view of photocell 11 relatively high on the gradient filter so that the intensity at photocell 11 is highest for that particular scan, with the intensities at photocells 9–10 and 12–14 being greater than I (gray) but less than that of photocell 11. In the same manner, fields of view at photocells 7 and 8 will be reflected downwardly by the lower edge of bump 62 to a darker portion of the gradient filter, so that the intensities at photocells 7 and 8 are less than gray intensity I.

The resolution of camera 44 depends in part on the width of indicia irregularities in increments of container rotation, i.e. the number of camera scans per unit width, the distance D (FIG. 6) between indicia positions, and the axial length of the indicia irregularities in relation to the number of camera elements. In a preferred embodiment of the invention (FIG. 6) wherein the indicia irregularities comprise circular bumps, the diameter of such bumps (i.e. length and width) is about 0.080 inches (FIG. 7). The distance D between indicia position is 0.104 inches, and the scan increments (FIG. 9) are equal to 0.0065 inches, yielding sixteen scans between adjacent indicia position centers and twelve scans across each bump 62. Effective separation S (FIG. 7) between photocells at the container surface is 0.013 inches.

Resolution also depends upon the angle of light source 32 and camera 44 to bumps 62 and thus to the container axis. For example, if the light source and camera are positioned too low, it is possible that the upper slope of the bump will reflect the field of view of one or more camera photocells over the gradient filter rather than to a bright upper portion thereof. In such an eventuality, the bump image would appear as in FIG. 10, with a dark region 62c where the brightest portion of the image should appear. Preferably, light source 32 and camera 44 are made adjustable as an assembly for empirical adjustment to obtain an acceptable image. Another marginal detection condition is illustrated in FIG. 13, wherein the dot image is generally dark with only a small bright spot 62d just above center. An image of this type, which is still detectable, may result from an accumulation of material in the container mold so that the dot bumps are not as sharp or pronounced as desired.

Figures 11, 12:
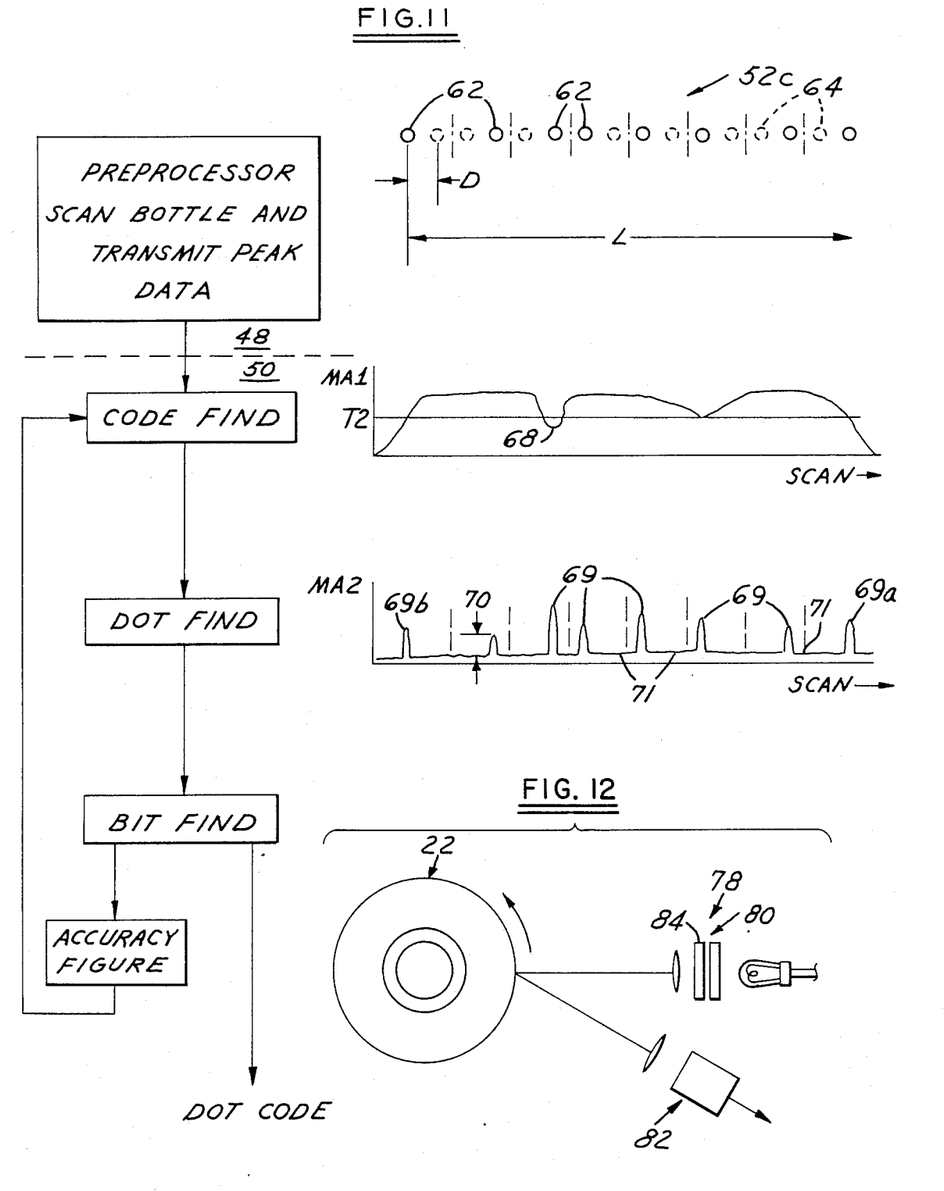
FIG. 11 is a flow chart with accompanying graphic illustrations showing operation of the scan and read method of the invention.
FIG. 12 is a fragmentary schematic diagram of a modification to the system of FIG. 1.

Operation of preprocessor 48 and main processor 50 (FIG. 1) will be best understood with reference to FIG. 11. The code 52c illustrated in FIG. 11 is the same as that illustrated in FIG. 6. The nominal arcuate length L between bumps 62 at the beginning and end of the start and end codes is predetermined. Likewise, the nominal distance D between indicia positions is known. Preprocessor 48 identifies the camera photocell receiving peak light intensity in each camera scan. This is accomplished by comparing each cell intensity with that of a selected lower cell, preferably the fourth lower cell, and identifying a peak intensity change. That is, the intensity of cell 5 is compared with that at cell 1, the intensity at cell 6 is compared with that at cell 2, and so on. The differential of four is selected as a function of bump size. Thus, in the scan of FIGS. 7 and 8, the peak differential is associated with cell 11 (i.e., cell 11 compared with cell 7). If this differential is greater than an empirically selected threshold T1, the absolute value of such peak differential, together with the associated cell number (11) and the scan number, is transmitted to main processor 50. This process is repeated at each scan increment for an entire container rotation. Thus, at the end of one rotation, there is stored in the memory of processor 50 a block of data representing peak differential intensity data (above differential threshold T1), and scan and cell numbers associated with such peak data. The task of main processor 50 is to distinguish a legitimate code from other irregularities, such as raised letters 66 (FIG. 1) on the container heel, and to read such code.

This is accomplished in main processor 50 by first finding blocks of data having an arcuate length and intensity pattern which might indicate a legitimate code, i.e., CODE FIND (FIG. 11). A moving average MA1 is obtained by summing at each scan increment all peak intensity differentials for a group of 4D adjacent scans. The moving average MA1 for each data block (only the legitimate data block is ilustrated in FIG. 11) is then analyzed to find one (or more) which has an amplitude greater than a preselected threshold T2 for a duration between 0.9L and 1.1L, with no dips 68 below threshold T2 of more than 2D duration. All peak intensity differential data blocks which satisfy these criteria are analyzed further to find individual code dots.

To locate individual code dots, a second moving average MA2 is obtained by again summing peak intensity differential data at each scan increment, this time over a group of ½D adjacent scans, i.e., DOT FIND (FIG. 11). Because of the narrower summing range (i.e., ½D compared with 4D), code dots or apparent dots will appear as peaks 69 above a "gray" background intensity 71. Start and end data bumps are then preliminarily identified at peaks 69a, 69b, and moving average MA2 is scanned in increments of D to identify presence or absence of a dot at each indicia position. (It will be recalled that potential dot positions are of known uniform spacing D, so that peaks 69 indicative of potential dot-code information should be at increments of D between start and each peaks 69a, 69b.) Any dot data so located is then paired to find code bits, i.e., BIT FIND (FIG. 11) which identifies the binary code indicative of mold of origin.

Most preferably, for increased reliability, the CODE FIND, DOT FIND and BIT FIND steps of FIG. 11 are carried out in an iterative process, with an ACCURACY FIGURE being determined for each data block that might represent a legitimate code, and the data block having the highest ACCURACY FIGURE being identified as the dot code. This ACCURACY FIGURE is obtained by examining the second moving average MA2 for each data block after the BIT FIND step to find the bit pair having the smallest amplitude differential. In the example of FIG. 11, the smallest differential is illustrated at 70. Such minimum differentials for each data block are compared, and the data block having the highest minimum bit pair differential is identified as indicating the dot code. A similar process may be employed for the code embodiments of FIGS. 3-5.

As previously indicated, disposition of gradient filter 40 (FIG. 1) such that transmissivity increases upwardly functions in accordance with the invention to detect the upper slope of the dot or bar protrusions. Thus, all of the embodiments of FIGS. 3-5 would appear substantially identically to the camera and detection electronics. The embodiments of FIGS. 3 and 5 could also be read with the transmissivity of the gradient filter increasing in the downward direction so that the system would detect lower slope of the protrusions. The embodiment of FIG. 4 could not be so read since the lower slopes are aligned, so that long and short bars would appear the same to the camera. Of course, the embodiment of FIG. 6 could be read either way.

FIG. 12 illustrates a modification 78 whereby the system detects and is responsive to the side edges or slopes of the protrusions. Light source 80 and camera 82 are positioned side-by-side, and the gradient filter 84 of light source 78 has a transmissivity characteristic which varies laterally—i.e. in the direction of container motion—rather than in the direction of the container axis. The array of photocells in camera 82 is coplanar with the container axis as in the embodiment of FIG. 1 so as to extend across the code area on the container heel. The "image" of dots 62 "seen" by camera 82 will be the same as that illustrated in FIG. 9 rotated 90° clockwise. Thus, the orientations of the gradient filter and lamp/camera combination determines the protrusion edge which will be detected. The embodiment of FIG. 12 is preferred for amber glass. The embodiment of FIG. 1 is preferred for flint glass where internal reflections may cause a "hot spot" problem with the embodiment of FIG. 12. The invention is also useful for reading codes on non-circular containers such as flasks or square bottles. The code may be molded onto the heel beneath a substantially flat container wall and read by moving the container linearly past a read station.

Figure 14:
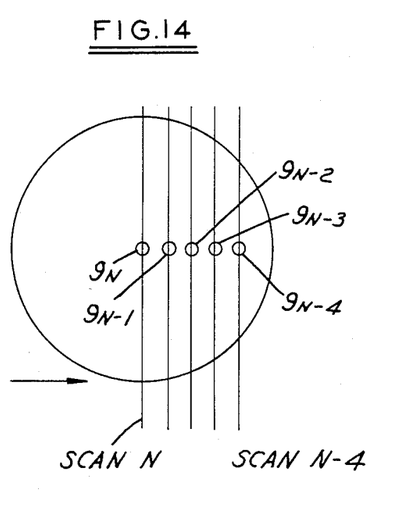
FIGS. 14 and 15 are illustrations respectively similar to FIGS. 7 and 8, and depict operation of another modified embodiment of the invention.
Figure 15:
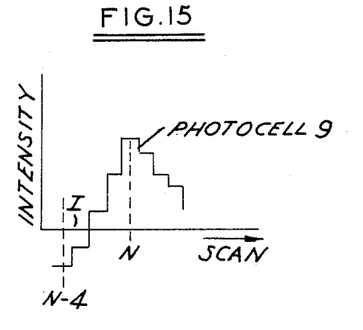

The embodiment of the invention hereinabove discussed, wherein the intensity at each camera cell is compared with the intensity at the fourth lower cell in each scan, is preferred in theory. However, it has been found the elements 1-16 of differing cameras 44 are not always sufficiently closely matched to yield reliable data. Thus, for example, if the temperature characteristic of cell 11 differs from that of cell 15, a peak differential may be indicated at cell 15 even though no such differential has in fact occurred. When the camera cells are not sufficiently closely matched, the technique of the invention may still be implemented in the manner illustrated in FIGS. 14 and 15. More specifically, intensity data is stored by cell in preprocessor 48 for four consecutive scans, with the oldest scan data being discarded when each new scan is taken. The intensity at each cell in a given scan is then compared with the intensity at the same cell in the fourth preceding scan. Thus, in the illustration of FIGS. 14-15, the intensity at cell 9 at scan N is compared with the intensity at the same cell at scan N-4, and the peak differential (FIG. 15) is thus identified. The remainder of the process—i.e., CODE FIND, DOT FIND and BIT FIND, remain as previously described.

A disadvantage of the code embodiment of FIG. 6 as compared with those of FIGS. 3-5 is that, because of the necessity of START and END bits, a lesser maximum code value is possible for a given number of indicia positions (sixteen in all FIGS. 3-6). This limitation can be overcome to some extent by grouping the indicia positions in sets of more than two. For example, in the embodiments thus far discussed, each set of two indicia positions can have either of two binary values (0 or 1), and two sets of four adjacent positions can have a total of four possible binary values (00, 01, 10 or 11). If the indicia positions are grouped in sets of four, with the limitation that each set must contain two dots (D) and two blank spaces (B), the following six combinations are possible:

B B D D
B D B D
B D D B
D B B D
D B D B
D D B B.

SUMMARY OF THE DISCLOSURE

Thus, in accordance with the a first aspect of the disclosure and invention, a molded container, preferably a molded glass container, is provided with coded indicia indicative of the mold of origin in the form of a plurality of irregularities extending in an array along a preselected location on the container outer surface, preferably in a circumferential array around the container heel. In each of the embodiments of FIGS. 3–6, the irregularities comprise outwardly projecting bumps or protrusions disposed at selected indicia positions, such positions being uniformly spaced around the heel. In each embodiment, the indicia are provided in two mutually unique sets at sequential pairs of positions, the two sets being the lateral mirror image of each other and thus being adapted to represent binary characters which collectively comprise a binary code indicative of the mold of origin.

In the embodiment of FIGS. 3–5, a bump or protrusion is provided at each indicia position, with the two bumps or protrusions of each set having differing dimension or positioning in the direction of the container axis so as to be distinguishable from each other. In FIGS. 3 and 5, the protrusions are identical and are offset in each set axially of the container. In FIG. 4, the protrusions are non-identical within each set. The embodiments of FIGS. 3–5 have the advantage of not requiring start and end bits at the ends of the code. In the preferred embodiment of FIG. 6, a protrusion is provided at only one of the two indicia positions within each paired-position set, the other position being "blank". The protrusions are aligned circumferentially of the container axis and are all identical. The embodiment of FIG. 6 has the advantage of requiring less memory within the processing electronics.

In accordance with a second aspect of the disclosure and invention, a system and method are provided for scanning and identifying the container code. The system includes a source of diffused light directed onto the container heel and having a light intensity gradient which varies in a predetermined direction with respect to the container axis. For flint glass, it is preferable that the intensity gradient of the light source vary in the direction of the container axis so that the system functions to detect upper slopes of the code bumps, and so that light energy reflected from internal surfaces is directed out of the camera field of view. For amber glass, it is preferred that the gradient be lateral to the container axis so that the system is responsive to side slopes of the code bumps.

A camera is positioned to receive light energy reflected by the container heel. The camera includes an array of light sensitive elements, preferably sixteen, perpendicular to the code array and, thus, coplanar to the container axis where the code extends circumferentially around the container heel. The container code is moved past the container field of view, by rotating the container in the case of the usual cylindrical container or by linear motion where the code is on the flat portion of a flask-type container. A preprocessor scans the camera array at increments of container motion.

In accordance with the method of the invention described in detail in connection with FIG. 11, peak illuminance data is transmitted at scan increments by the preprocessor to a main processor. In the main processor, blocks of peak data are analyzed in an iterative process to first locate data blocks which might represent the container code, then to identify individual code bumps or irregularities, and then to associate such irregularities by pairs of indicia positions so as to identify possible code bits. These code bits are then analyzed to identify the data block most likely to represent an actual code, and the actual code is then determined.

The invention claimed is:

1. A molded container having a body and a central axis extending longitudinally therethrough, said body being formed in a mold and having a sidewall, a bottom load-bearing surface, a heel portion of the sidewall contiguous with the bottom, and integral indicia for identifying the mold in which the said container was formed, said integral indicia comprising a plurality of generally radially oriented surface irregularities extending in an array generally perpendicular to the central axis at a series of circumferential positions on the heel, said circumferential positions being uniformly spaced from each other along said heel and disposed in sets of two circumferentially adjacent positions, there being at least one of said irregularities in each of said sets of two circumferentially adjacent positions, said sets being in mutually unique pairs of adjacent circumferential positions, each of said sets being readable as a unique bit of binary information which depends upon the positional sequence of said irregularities within said set, and said sets collectively identifying the mold in which said container was formed.

2. The molded container of claim 1 wherein each of said sets comprises one irregularity at either one of the two circumferential positions therein.

3. The molded container of claim 1 wherein each of said sets comprises two irregularities having different axial positions.

4. The molded container of claim 1 wherein each of said sets comprises two irregularities having different dimensional characteristics.

5. A method of identifying a molded container having side and end walls and a central axis with a mold of origin comprising the steps of:
(a) molding into each said container a code indicative of the mold of origin, said code comprising a plurality of surface irregularities extending in a lineal array along the heel of said container perpendicularly of said axis at the junction of the container side and end walls, said irregularities being disposed at indicia positions around said heel in mutually unique sets at pairs of circumferentially adjacent positions, each said set being readable as a unique bit of binary information which depends upon sequence of irregularities within said set and which collectively identify said mold of origin,
(b) directly a source of diffused light energy onto the container heel, said source having an non-uniform intensity gradient which varies as a predetermined function of direction across said source,
(c) moving said container heel with respect to said source in the direction of said lineal dimension such that said array sweeps past said source,
(d) positioning a camera to continually receive light energy from said source reflected by said heel, including said array, as said container is moved, and
(e) identifying said code indicative of mold of origin as a function of variations in light reflected from said heel caused by said irregularities by reading irregularities associated with each said pair of circumferentially adjacent positions as a bit of binary information which collectively comprises said code.

6. The method set forth in claim 5 wherein said step (a) comprises the step of molding said code as a plurality of radially outwardly facing surface irregularities extending in an array along said heel, and
wherein said step (e) comprises the step of identifying said code as a function of variatons in continuously light reflected from said source caused by each said irregularity.

7. A method of reading a code indicative of mold of origin on a molded container which includes side and end walls, and a heel on said side wall at the junction of said side and end walls, said code comprising a plurality of discrete protrusions extending in a lineal array along said heel, said method comprising the steps of:
  (a) directing a source of diffused light energy onto the container heel, said source having a width-wise dimension and an intensity gradient which varies across said dimension,
  (b) positioning a camera to have a field of view which includes said heel and which is continually reflected by said heel and by indicia contained thereon onto said source,
  (c) moving said container heel with respect to said source and camera such that said protrusions successively intersect said field of view and vary reflection of said field of view across said dimension of said source, whereby intersection of said protrusions with said field of view alters the intensity of light viewed by said camera from said source, and
  (d) reading said code as a function of said intensity alterations.

8. The method set forth in claim 7 wherein said camera comprises a linear array of light sensitive elements; wherein said step (b) comprises the step of positioning said camera such that said field of view of said element array extends perpendicularly of said lineal protrusion array along said heel; and wherein said step (c) comprises the step of moving said container heel in the direction of said lineal protrusion array and perpendicularly of said camera element linear array.

9. The method set forth in claim 8 wherein said step (d) comprises the steps of:
  (d1) scanning said array of light sensitive elements at increments of container motion,
  (d2) storing data as a function of variations in light intensity at said element array at increments of container motion,
  (d3) identifying from said data stored in step (d2) a data block indicative of said code,
  (d4) identifying within said block data indicative of individual ones of said protrusions, and then
  (d5) correlating said data indicative of individual ones of said protrusions to identify said code.

10. The method set forth in claim 9 wherein said code protrusions are disposed at at least some of a plurality of uniformly spaced indicia positions, and
  wherein said step (d5) comprises the step of correlating said data indicative of individual protrusions as a function of pairs of circumferentially adjacent indicia positions, correlating occurrence of protrusions at pairs of adjacent positions with a binary code bit, and then identifying said code indicative of mold of origin from protrusions at collective sequential circumferential pairs of said positions.

11. The method set forth in claim 10 wherein said step (d2) comprises the step of comparing light intensity at each said element of said array at each increment of container motion with intensity at another element of said array at the same said increment.

12. The method set forth in claim 10 wherein said step (d2) comprises the step of comparing light intensity at each element of said array at each increment of container motion with intensity at the same said element in said array at a preselected number of preceding scan increments.

13. The method set forth in claim 12 wherein said preselected number is four.

14. A system for reading a code on a molded container indicative of mold of origin, said container comprising side and end walls, a container axis, and a container heel at the junction of said side and end walls, said code comprising a plurality of discrete protrusions projecting outwardly of said side wall at said heel and extending in a lineal array along said heel, said system comprising
  a source of diffused light energy having a widthwise dimension across said source and an intensity gradient which varies across said dimension,
  means for moving said container heel in the direction of said dimension across said source,
  a camera including a linear array of light sensitive elements coplanar with said container axis positioned to have a field of view at said heel, said camera being so oriented with respect to said source and said moving means that said field of view is continually reflected by said heel onto said source, passage of a said protrusion through said field of view altering reflection of said field of view with respect to said dimension across said source, and
  means for reading said code as a function of said reflection alterations.

15. The system set forth in claim 14 wherein said intensity gradient varies across said source in the direction of said axis.

16. The system set forth in claim 14 wherein said intensity gradient varies across said source perpendicularly of said axis.

* * * * *